United States Patent
Franer et al.

(10) Patent No.: US 7,677,392 B2
(45) Date of Patent: Mar. 16, 2010

(54) TROCAR ASSEMBLY TIP PROTECTOR

(75) Inventors: Paul T. Franer, Cincinnati, OH (US); Thomas A. Gilker, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1216 days.

(21) Appl. No.: 11/217,673

(22) Filed: Sep. 2, 2005

(65) Prior Publication Data
US 2006/0021891 A1 Feb. 2, 2006

Related U.S. Application Data

(63) Continuation-in-part of application No. 10/943,219, filed on Sep. 17, 2004.

(60) Provisional application No. 60/506,725, filed on Sep. 30, 2003.

(51) Int. Cl.
*A61B 17/06* (2006.01)
*B65D 83/10* (2006.01)
*B65D 69/00* (2006.01)

(52) U.S. Cl. .................. 206/438; 206/363; 206/571

(58) Field of Classification Search .............. 206/443, 206/363, 370, 372, 571, 589, 373, 486, 438
See application file for complete search history.

(56) References Cited

U.S. PATENT DOCUMENTS

| | | | | |
|---|---|---|---|---|
| 2,651,407 A | * | 9/1953 | Blackman | 206/366 |
| 3,227,265 A | * | 1/1966 | Schneider | 206/382 |
| 3,727,749 A | | 4/1973 | Martin | |
| 4,163,493 A | * | 8/1979 | Current | 206/380 |
| 5,024,326 A | * | 6/1991 | Sandel et al. | 206/366 |
| 5,090,564 A | * | 2/1992 | Chimienti | 206/365 |
| 5,279,578 A | * | 1/1994 | Cooke | 604/192 |
| 5,311,985 A | * | 5/1994 | Suida | 206/210 |
| 5,375,717 A | | 12/1994 | Roshdy | |
| 5,485,917 A | * | 1/1996 | Early | 206/363 |
| 5,702,270 A | | 12/1997 | Casica et al. | |
| 5,704,495 A | | 1/1998 | Lyons et al. | |
| 5,762,202 A | | 6/1998 | Atad | |
| 5,975,295 A | * | 11/1999 | Diamond | 206/366 |
| 6,279,743 B1 | * | 8/2001 | Ballard et al. | 206/364 |
| 6,648,899 B2 | * | 11/2003 | Kalinski et al. | 606/148 |
| 6,783,003 B2 | * | 8/2004 | Simm et al. | 206/366 |
| 2002/0014560 A1 | * | 2/2002 | Diamond | 248/37.3 |
| 2002/0063074 A1 | * | 5/2002 | Simm et al. | 206/366 |
| 2003/0121811 A1 | | 7/2003 | Roshdy | |
| 2003/0196922 A1 | | 10/2003 | Reaux | |

* cited by examiner

*Primary Examiner*—Ehud Gartenberg
*Assistant Examiner*—Jose S Stephens, III

(57) ABSTRACT

A packaging device for a trocar assembly includes a housing member having a compliant first sleeve adapted for selective frictional retention of a trocar assembly component relative to the housing member and a compliant second sleeve adapted for selective frictional retention of a trocar assembly component relative to the housing member. The first sleeve includes an inlet opening at a first end thereof and a closed second end defining a shield member positioned about a tip of a trocar assembly component positioned therein. The second sleeve includes an inlet opening at a first end thereof and a closed second end defining a shield member positioned about a tip of a trocar assembly component positioned therein.

9 Claims, 4 Drawing Sheets

TROCAR ASSEMBLY TIP PROTECTOR

CROSS REFERENCE TO RELATED APPLICATION

This application is continuation-in-part of U.S. patent application Ser. No. 10/943,219, filed Sep. 17, 2004, entitled "TROCAR ASSEMBLY TIP PROTECTOR", which is currently pending, and is based upon U.S. Provisional Patent Application No. 60/506,725, filed Sep. 30, 2003, entitled "TROCAR ASSEMBLY TIP PROTECTOR".

BACKGROUND OF THE INVENTION

1. Field of the Invention

The invention relates to packaging devices for trocar assemblies. More particularly, the invention relates to a trocar assembly packaging device providing for protection from and for the tips of the trocar sleeve and obturator.

2. Description of the Prior Art

A trocar assembly is a surgical instrument that is used to gain access to a body cavity. A trocar assembly generally comprises two major components, a trocar sleeve, composed of a trocar housing and a trocar cannula, and a trocar obturator. The trocar sleeve, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar sleeve is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar sleeve is inserted through the perforation made by the obturator and the obturator is withdrawn, leaving the trocar sleeve as an access way to the body cavity.

The proximal end portion of the trocar sleeve is typically adjoined by a housing that defines a chamber having an open distal end portion that communicates with the interior lumen defined by the trocar sleeve. An obturator, or other elongated surgical instruments, axially extend into and are withdrawn from the trocar sleeve through the proximal end portion of the chamber. Trocar obturators are typically designed with a sharp tip that is used to puncture the abdominal wall. Trocar packaging designs much ensure that the sharp tip of the trocar obturator does not puncture the packaging material that forms the sterile barrier. If the material used for the sterile barrier is not strong enough to prevent puncture on its own, an ancillary form of protection is required.

Typically, a tip protector is used for trocar assemblies, especially trocar obturators. Current tip protectors generally consist of a cap that completely encapsulates the sharp tip of the trocar obturator. Such caps completely obscure the view of the tip of the trocar obturator as it sits in the unopened package. It is, however, important for those using these instruments to be able to visibly identify the tip style prior to use. This is especially important when a variety of different obturator tip styles are available.

In addition to the tip problem discussed above, problems exist when providing packaging for surgical trocar assemblies. Some trocar assembly designs require that the trocar assembly be packaged with the obturator not inserted into the trocar sleeve. If this is the case, a two-piece device assembly must be packaged.

Surveys of operating room nurses responsible for removing trocar assemblies from their packages reveal that nurses prefer to dispense a single assembly from the trocar assembly package rather than a two-piece assembly. Reasons for preferring a one-piece assembly include reducing the opportunity for components to roll off from the sterile field as well as the desire to keep the obturator and trocar sleeve matched up together when dispensing or unpacking numerous different trocar types.

As a result, it is readily apparent that a trocar assembly packaging device is needed which overcomes the shortcomings of prior trocar assembly packaging devices. The present invention provides such a trocar assembly packaging device.

SUMMARY OF THE INVENTION

It is, therefore, an object of the present invention to provide a packaging device for a trocar assembly that includes a housing member having a compliant first sleeve adapted for selective frictional retention of a trocar assembly component relative to the housing member and a compliant second sleeve adapted for selective frictional retention of a trocar assembly component relative to the housing member. The first sleeve includes an inlet opening at a first end thereof and a closed second end defining a shield member positioned about a tip of a trocar assembly component positioned therein. The second sleeve includes an inlet opening at a first end thereof and a closed second end defining a shield member positioned about a tip of a trocar assembly component positioned therein.

It is also an object of the present invention to provide a packaging device for a trocar assembly that includes a housing member having a first sleeve adapted for selective frictional retention of a trocar assembly component relative to the housing member and a second sleeve adapted for selective frictional retention of a trocar assembly component relative to the housing member. The first sleeve includes an inlet opening at a first end thereof and a closed second end defining a shield member positioned about a tip of a trocar assembly component positioned therein. The second sleeve includes an inlet opening at a first end thereof and a closed second end defining a shield member positioned about a tip of a trocar assembly component positioned therein. The second end of the second sleeve includes an obliquely angled surface relative to a longitudinal axis of the second sleeve shaped and dimensioned to mate with a tip of a trocar assembly component.

It is another object of the present invention to provide a trocar assembly including a packaging device. The assembly includes a trocar sleeve having a trocar sleeve tip, a trocar obturator having a trocar obturator tip and a housing member including a first sleeve adapted for selective retention of the trocar obturator along a first longitudinal axis and a second sleeve adapted for selective retention of the trocar sleeve along a second longitudinal axis. The first sleeve and the second sleeve respectively include closed second ends defining shield members protecting the trocar obturator tip and the trocar sleeve tip, the shield members lying in a shield longitudinal axis which is substantially perpendicular to the first and second longitudinal axes and the trocar obturator tip and the trocar sleeve tip are respectively positioned adjacent the shield member.

Other objects and advantages of the present invention will become apparent from the following detailed description

DESCRIPTION OF THE PREFERRED EMBODIMENT

Figure 1:
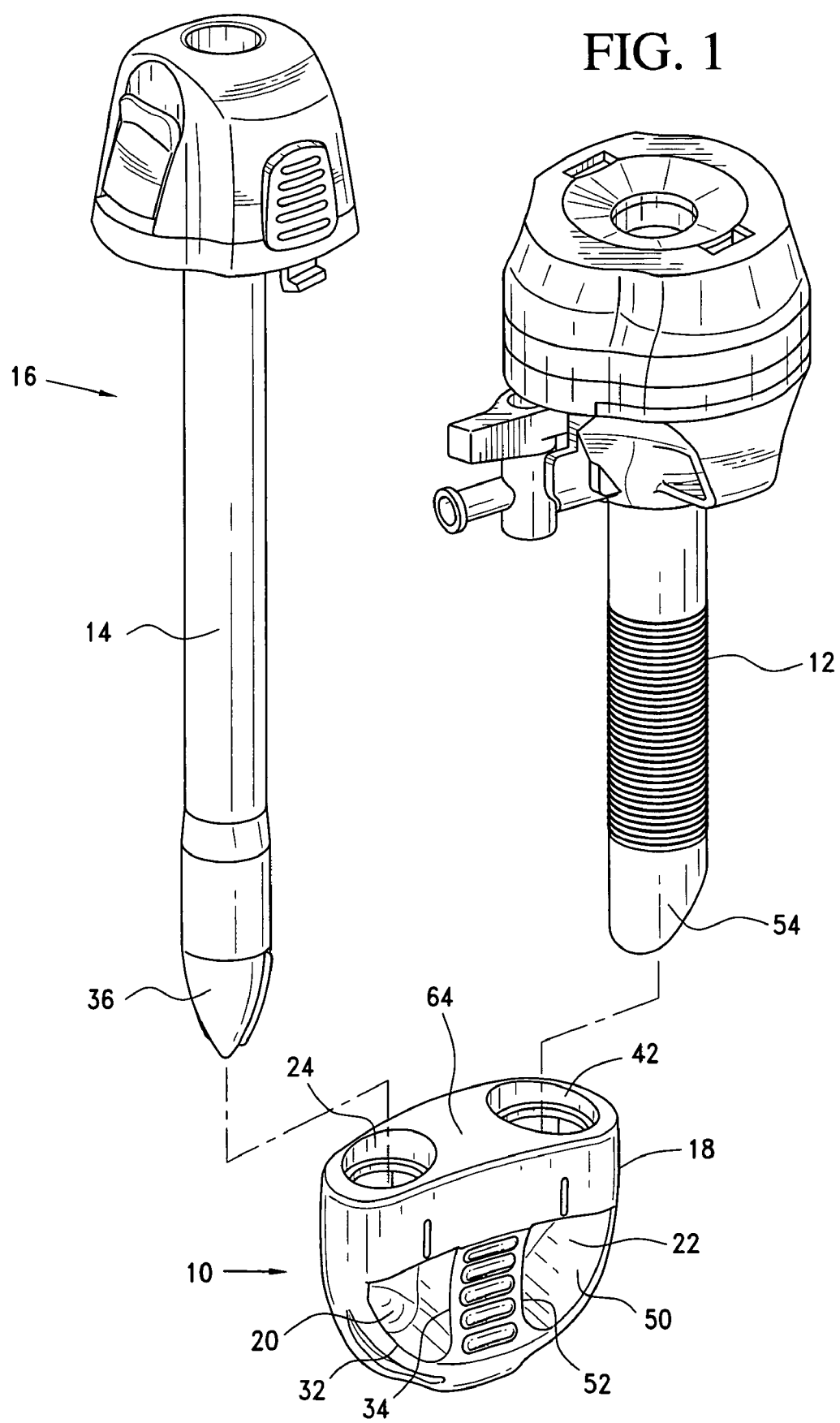
FIG. 1 is an exploded perspective view of the present packaging device with a trocar sleeve and trocar obturator.
Figure 3:
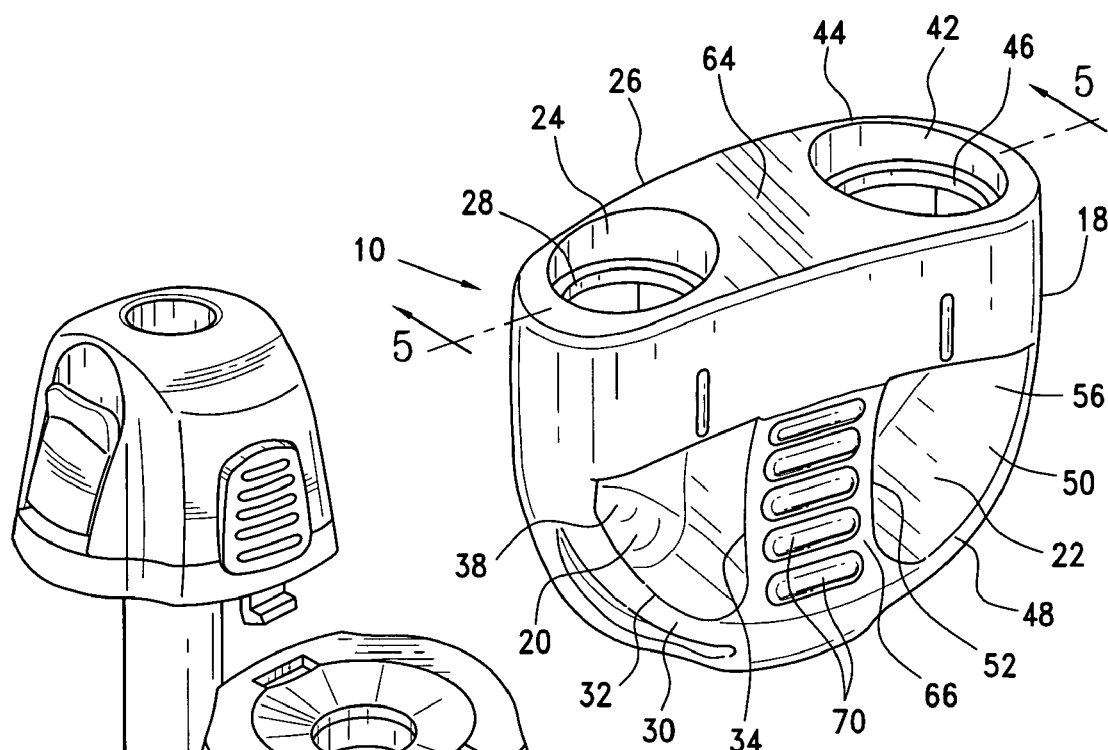
FIGS. 3 and 4 are detailed perspective views of the front and back of the packaging device.
Figure 2:
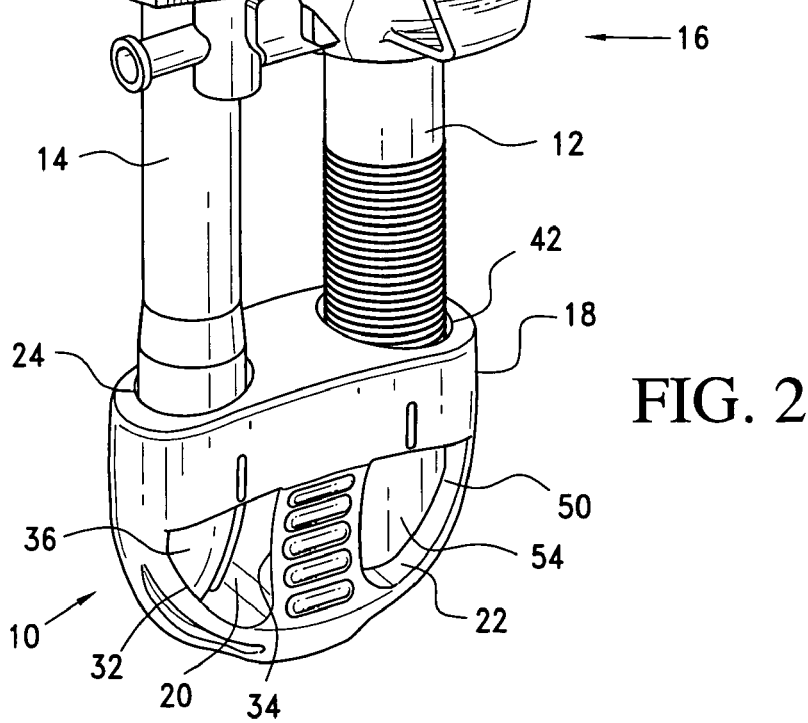
FIG. 2 is a perspective view of the present packaging device with a trocar sleeve and trocar obturator.
Figure 4:
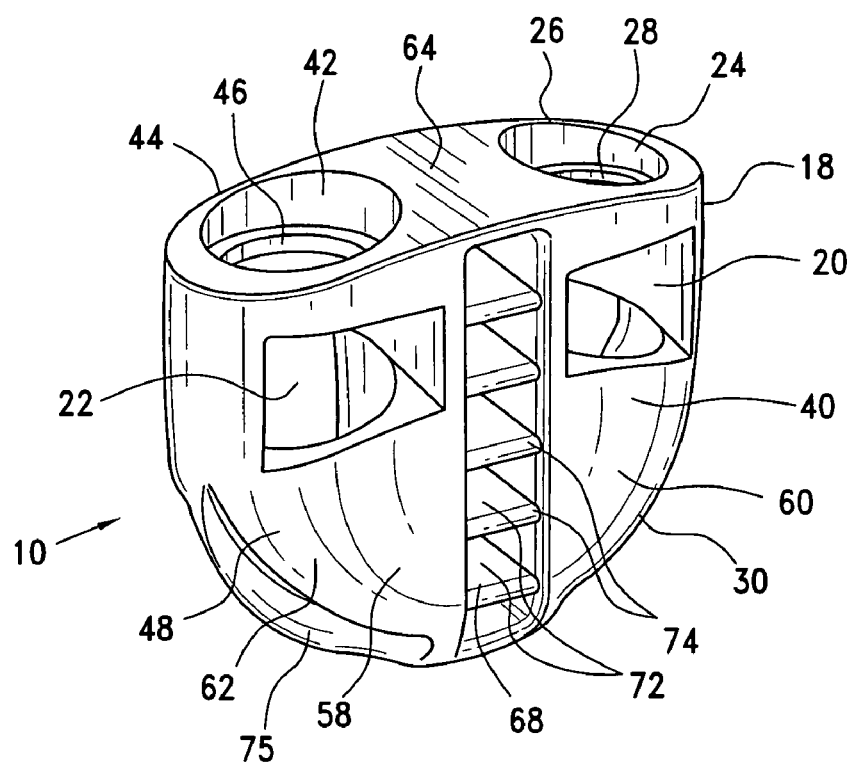
Figure 5:
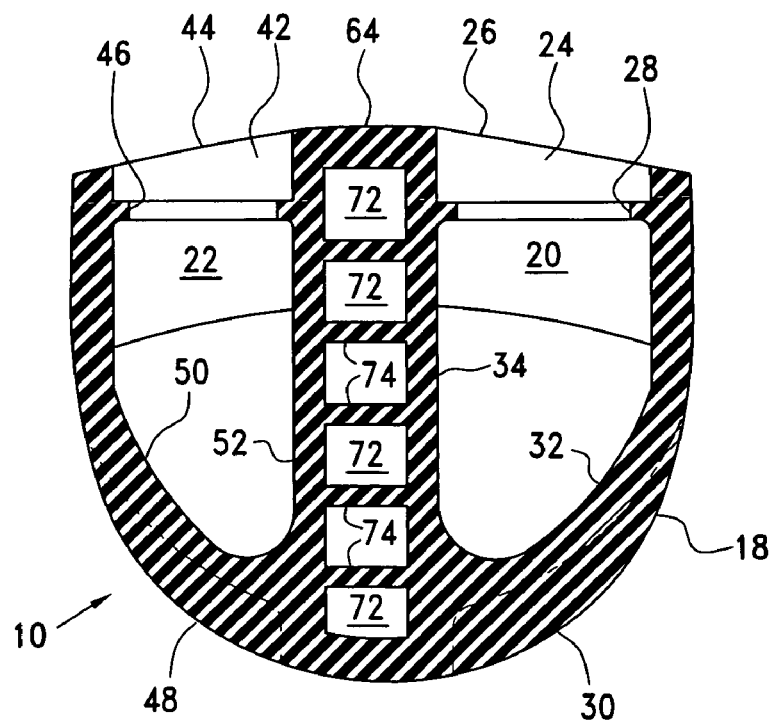
FIG. 5 is a cross sectional view of the packaging device.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 5, a packaging device 10 for trocar assembly components, for example, a trocar sleeve 12 and a trocar obturator 14 of a trocar assembly 16, is disclosed. The packaging device 10 includes a molded plastic housing member 18 that serves as a tip protector for trocar assemblies. The packaging device 10 further supports the trocar obturator 14 adjacent the trocar sleeve 12 in a convenient manner.

The present packaging device is particularly design for use in conjunction with larger diameter trocar assemblies. For example, the present packaging device was developed for 7 mm to 12 mm diameter trocars, although the concepts underlying the present packaging device could certainly be used with 5 mm diameter trocars. Ultimately, the packaging device is not size dependent and each design will be capable of accommodate a limited range of trocar diameters, for example, 11 mm and 12 mm diameter trocars, in a single device based upon the compliance of the material used and, in particular, the compliance of the internal lip discussed below in greater detail. With this in mind, it is contemplated the compliance will be in the range permitting diametric expansion on the order of approximately 2 to 3 mm. In accordance with a preferred embodiment of the present invention, the entire housing member of the packaging device is molded from a compliant material, for example, an elastomer. While the present packaging device is disclosed in accordance with a preferred embodiment as being constructed from a particular material, those skilled in the art will appreciate the packaging device may be manufactured from a variety of similar materials without departing from the spirit of the present invention.

The packaging device 10 includes a unitary housing member 18 with adjacent retaining members, for example, substantially parallel first and second sleeves 20, 22, formed within housing member 18. The first and second sleeves 20, 22 are integrally formed with the housing member 18 and are, therefore, connected in a manner that maintains the trocar sleeve 12 and trocar obturator 14 in a predefined relationship when both are mounted within the packaging device 10. As those skilled in the art will certainly appreciate, trocar sleeves 12 are slightly larger in diameter than the trocar obturators 14 that pass therethrough. With that in mind, the first and second sleeves 20, 22 of the present packaging device 10 are different sizes, with the first sleeve 20 being slightly smaller than the second sleeve 22 such that the first sleeve 20 is designed to accommodate the trocar obturator 14 and the second sleeve 22 is designed to accommodate the trocar sleeve 12.

The first sleeve 20 includes an inlet 24 adjacent the first end 26 of thereof. The inlet 24 is formed with an internal lip 28 shaped and dimensioned to frictional engage the trocar obturator 14, for example, as it is positioned within the packaging device 10. Because the packaging device 10, including the internal lip 28 is formed of compliant material, the first sleeve 20 will accommodate a variety of instrument diameters while still functioning in accordance with the underlying concepts of the present invention. In fact, the range of trocar instruments which may be accommodated by a single mold in accordance with the present invention can be easily varied by simply changing two core pins in the mold. In particular, a single mold base can be modified in lieu of making an entirely new mold by replacing two component parts of that mold (that is, the core pins) to alter the effective trocar diameter the packaging device can accommodate.

Figure 6:
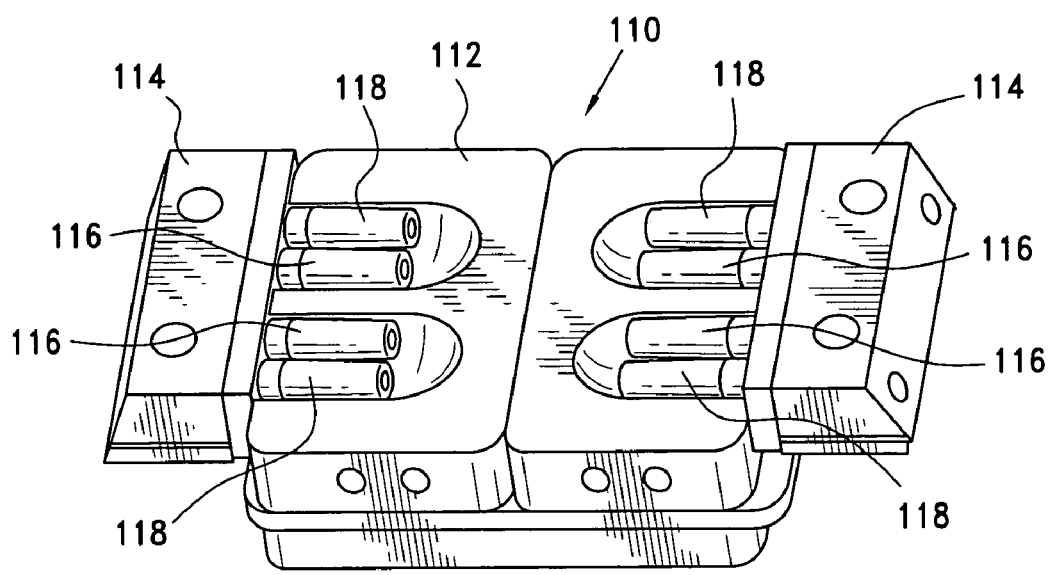
FIG. 6 is a top plan view of a mold for use in accordance with the present invention.
Figure 7:
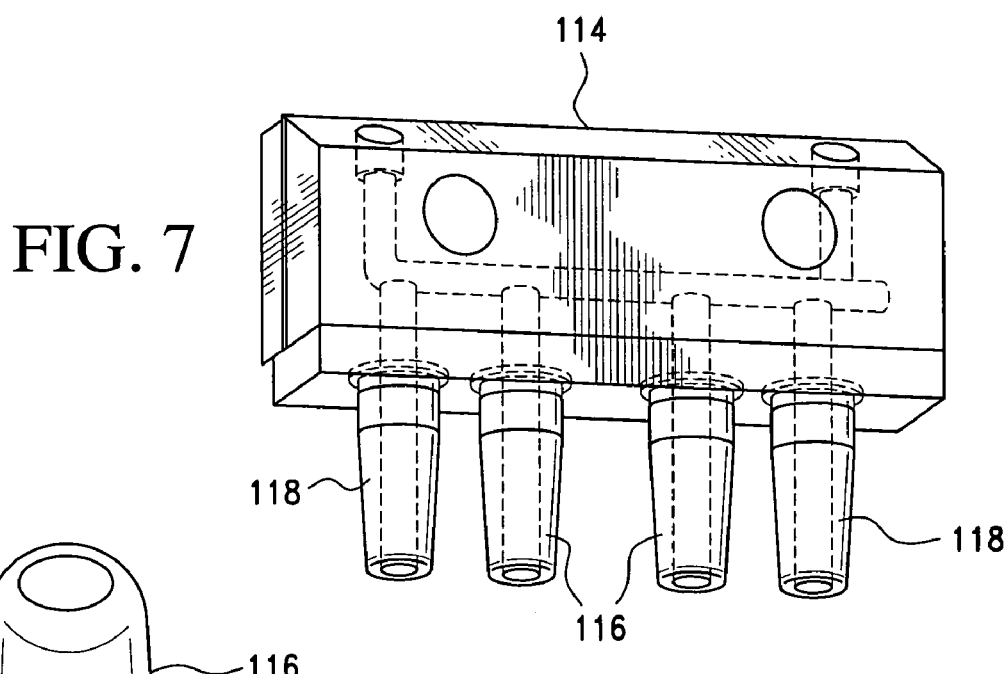
FIG. 7 is a detailed perspective view of the secondary mold member.
Figure 8:
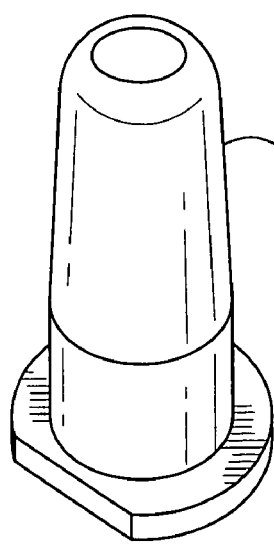
FIG. 8 is a detailed perspective of an insert used in conjunction with the secondary mold member.

More particularly, and with reference to FIGS. 6, 7 and 8, a preferred mold 110 for the present packaging device 10 is shown. The mold 110 includes a primary mold member 112 and a secondary mold member 114. The secondary mold member 114 is selectively coupled to the primary mold member 112 to achieve the provision of a complete mold 110 for the injection molding of the present packaging device 10.

The secondary mold 114 includes first and second selectively replaceable core pins 116, 118. The first and second core pins 116, 118 respectively define the shape and size of the first and second sleeves 20, 22. As such, by simply replacing the first and second core pins 116, 118 the size (and shape) of the first and second sleeves 20, 22 may be readily varied without the need for the creation of an entirely new mold.

Referring back to FIGS. 1-5, the second end 30 of the first sleeve 20 is closed and is formed with an obliquely angled surface 32 along one side and a substantially straight parallel surface 34 along the other side (both relative the longitudinal axis of the first sleeve 20 and the longitudinal axis of the inserted trocar obturator 14). The angled surface 32 is oriented to generally follow the shape of the obturator tip 36 along that side and provides an aesthetically pleasing appearance to the packaging device 10. By generally following the profile of the obturator tip 36, the angled surface 32 mates with the obturator tip 36 helping to maintain the trocar obturator 14 in a preferred orientation. The first sleeve 20 also includes front and rear surfaces 38, 40 adjacent the second end 30 thereof. In accordance with a preferred embodiment of the present invention, the front surface 38 is left open while the rear surface 40 is partially closed.

As with the first sleeve 20, the second sleeve 22 includes an inlet 42 adjacent the first end 44 of thereof. The inlet 42 is formed with an internal lip 46 shaped and dimensioned to frictional engage the trocar obturator 14, for example, as it is positioned within the packaging device 10. Because the packaging device 10, including the internal lip 46 is formed of compliant material, the second sleeve 22 will accommodate a variety of instrument diameters while still functioning in accordance with the underlying concepts of the present invention.

The second end 48 of the second sleeve 22 is closed and is formed with an obliquely angled surface 50 along one side and a substantially straight parallel surface 52 along the other side (both relative the longitudinal axis of the second sleeve 22 and the longitudinal axis of the inserted trocar sleeve 12). In fact, the shape of the second end 48 of the second sleeve 22 is a similar to that of the second end 30 of the first sleeve 20. The angled surface 50 is oriented to generally follow the beveled shape of the trocar sleeve tip 54 along that side and provides and aesthetically pleasing appearance to the packaging device 10. In particular, the angled surface 50 helps to maintain the trocar sleeve 12 in a preferred radial orientation to keep the stopcock from reaching a position that might endanger it, that is, rotated so it's sticking out sideways and possible subject to an impact. This is achieved by the fact the angled surface 50 mates with the trocar sleeve tip 54 and prevents the entire trocar sleeve 12 from rotating. The second sleeve 22 also includes front and rear surface 56, 58 adjacent the second end 48 thereof. In accordance with a preferred embodiment of the present invention, the front surface 56 is left open while the rear surface 58 is partially closed.

The generally open construction of the packaging device 10 adjacent the tips 54, 36 of the trocar sleeve 12 and trocar obturator 14 provides for open space around the components, which is necessary for gas sterilization and other purposes. The packaging device 10 is formed such that the tips 54, 36 of the trocar sleeve 12 and the trocar obturator 14 are covered only at their ends by the housing member 18, with partial cover along the backsides of the trocar obturator 14 and trocar sleeve 12 which are slightly covered by walls member 60, 62 formed along the partially closed rear surfaces 40, 58 of the respective first and second sleeves 20, 22. This open construction, in addition to enhancing sterilization, enhances viewing of the trocar sleeve 12 and the trocar obturator 14. Therefore, the front surfaces of the tips 54, 36 of the trocar sleeve 12 and trocar obturator 14 are unobscured and can easily be identified.

The present construction also provides protection for and from the tips 54, 36 of both the trocar sleeve 12 and the trocar obturator 14 and the closed second ends 30, 48 of the first and second sleeves 20, 22 function as stops for the respective tips 54, 36 of the trocar sleeve 12 and trocar obturator 14. The packaging device 10 further protects the tips 54, 36 from contacting the next layer of packaging material that may form a sterile barrier for the trocar assembly 16.

The housing member 18 includes a bridging section 64 between the first and second sleeves 20, 22. The bridging section 64 includes a front surface 66 and rear surface 68. The front surface 66 is slightly concave and is formed with protrusions 70 in a manner providing an ideal gripping surface for one using the present packaging device 10. The rear surface 68 is formed with internally directed recesses 72. The internally directed recessed 72 define ribs 74. The combination of the recesses 72 and ribs 74 help in reducing the weight of the housing member 18 while maintaining its structural stability.

The housing member 18 further includes ridges 75 along the forward end thereof. The ridges 75 provide for an additional textured surface allowing for easy gripping during instrument extraction from the packaging device 10. In fact, the entire external shape of the housing member 18 is optimized to enhance handling thereof.

In practice, and in accordance with a preferred embodiment a trocar sleeve 12 having a trocar sleeve tip 54 and a trocar obturator 14 having a trocar obturator tip 36 are placed within the packaging device 10 for sterilization, packaging, shipping and general use prior to removal of the trocar sleeve 12 and trocar obturator 14 for performance of a surgical procedure. The housing member 18 of the packaging device 10 includes the previously discussed first sleeve 20 adapted for selective retention of the trocar obturator 14 along a first longitudinal axis and the second sleeve 22 adapted for selective retention of the trocar sleeve 12 along a second longitudinal axis, the first and second longitudinal axes being substantially parallel. The closed second ends 30, 48 of the first sleeve 20 and the second sleeve 22 respectively shield the trocar sleeve tip 54 and the trocar obturator tip 36, the shield member, that is, the second ends 30, 48 of the first and second sleeves 20, 22, lying in a shield longitudinal axis which is substantially perpendicular to the first and second longitudinal axes and the trocar sleeve tip 54 and the trocar obturator tip 36 are respectively positioned adjacent the shield member.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A packaging device for a trocar assembly, comprising:
a trocar sleeve having a trocar sleeve tip; a trocar obturator having a trocar obturator tip; a housing member including a first sleeve adapted for selective frictional retention of a trocar assembly component relative to the housing member and a second sleeve adapted for selective frictional retention of a trocar assembly component relative to the housing member;
the first sleeve including an inlet opening at a first end thereof and a closed second end defining a shield member positioned about a tip of a trocar assembly component positioned therein;
the second sleeve including an inlet opening at a first end thereof and a closed second end defining a shield member positioned about a tip of a trocar assembly component positioned therein, the second end of the second sleeve includes an obliquely angled surface relative to a longitudinal axis of the second sleeve shaped and dimensioned to mate with a tip of a trocar assembly component;
wherein the first sleeve includes an opening between the first end and the second end and the second sleeve includes an opening between the first end and the second end, and wherein the first sleeve and the second sleeve are sufficiently compliant permitting diametric expansion on the order of approximately 2 to 3 mm.

2. The packaging device according to claim 1, wherein the second end of the first sleeve includes an obliquely angled surface relative to a longitudinal axis of the first sleeve shaped and dimensioned to mate with a tip of a trocar assembly component.

3. A trocar assembly including a packaging device, comprising:
a trocar sleeve having a trocar sleeve tip;
a trocar obturator having a trocar obturator tip;
a housing member including a first sleeve adapted for selective retention of the trocar obturator along a first longitudinal axis and a second sleeve adapted for selective retention of the trocar sleeve along a second longitudinal axis;
the first sleeve and the second sleeve respectively including closed second ends defining shield members protecting the trocar obturator tip and the trocar sleeve tip, the shield members lying in a shield longitudinal axis which is substantially perpendicular to the first and second longitudinal axes and the trocar obturator tip and the trocar sleeve tip are respectively positioned adjacent the shield members;

wherein the first sleeve includes an opening between the first end and the second end and the second sleeve includes an opening between the first end and the second end, and wherein the first sleeve and the second sleeve are sufficiently compliant permitting diametric expansion on the order of approximately 2 to 3 mm.

4. The trocar assembly according to claim 3, wherein the entire housing member is composed of an elastomer.

5. The trocar assembly according to claim 3, wherein the first sleeve and second sleeve respectively include inlet openings adjacent their first ends, and each of the inlet openings includes a lip shaped and dimensioned to frictionally engage a trocar assembly component positioned therein.

6. The trocar assembly according to claim 5, wherein the lips are compliant.

7. The trocar assembly according to claim 5, wherein a bridging member connects the first sleeve to the second sleeve such that the first and second longitudinal axes being substantially parallel.

8. The trocar assembly according to claim 3, wherein the second end of the second sleeve includes an obliquely angled surface relative to the second longitudinal axis shaped and dimensioned to mate with a tip of the trocar sleeve.

9. The trocar assembly according to claim 8, wherein the second end of the first sleeve includes an obliquely angled surface relative to the first longitudinal axis shaped and dimensioned to mate with a tip of the trocar obturator.

* * * * *